(12) United States Patent
Wong et al.

(10) Patent No.: US 8,338,564 B2
(45) Date of Patent: Dec. 25, 2012

(54) METHOD FOR THE PREPARATION OF PHYTOSTEROLS FROM TALL OIL PITCH

(75) Inventors: Alfred Wong, Vancouver (CA); Hugh Sven Oscar Norman, Prince George (CA); Angus Kirke MacMillan, Delta (CA)

(73) Assignee: Pharmachem Laboratories, Inc., Kearny, NJ (US)

( * ) Notice: Subject to any disclaimer, the term of this patent is extended or adjusted under 35 U.S.C. 154(b) by 0 days.

(21) Appl. No.: 12/850,016

(22) Filed: Aug. 4, 2010

(65) Prior Publication Data

US 2010/0305342 A1    Dec. 2, 2010

Related U.S. Application Data

(63) Continuation of application No. 12/233,392, filed on Sep. 18, 2008, now abandoned, which is a continuation of application No. 11/710,312, filed on Feb. 23, 2007, now abandoned, which is a continuation of application No. 10/964,792, filed on Oct. 14, 2004, now abandoned, which is a continuation of application No. 10/630,572, filed on Jul. 30, 2003, now abandoned, which is a continuation of application No. 09/601,762, filed as application No. PCT/CA99/00150 on Feb. 19, 1999, now abandoned.

(30) Foreign Application Priority Data

Feb. 20, 1998  (CA) .................................... 2230373

(51) Int. Cl.
- *C11B 13/00* (2006.01)
- *C11B 7/00* (2006.01)
- *A61K 31/56* (2006.01)

(52) U.S. Cl. .................... 530/205; 514/182; 554/195
(58) Field of Classification Search .................. 530/205; 514/182; 554/195
See application file for complete search history.

(56) References Cited

U.S. PATENT DOCUMENTS 4,076,700 A * 2/1978 Harada et al. ................. 530/206

FOREIGN PATENT DOCUMENTS

| CS | 256092 | * | 4/1988 |
| GB | 895145 | * | 5/1942 |

* cited by examiner

*Primary Examiner* — Nathan M Nutter
(74) *Attorney, Agent, or Firm* — Andrew D. Gerschutz; Michael G. Johnston; Moore & Van Allen PLLC

(57) ABSTRACT

A method of preparing phytosterols from tall oil pitch containing steryl esters comprises the steps of converting the steryl esters to free phytosterols while in the pitch to produce a modified pitch containing the free phytosterols; removing light ends from the modified pitch by evaporation to produce a bottom fraction containing the free phytosterols; evaporating the bottom fraction to produce a light phase distillate containing the free phytosterols; dissolving the light phase distillate in a solvent comprising an alcohol to produce a solution containing the free phytosterols; cooling the solution to produce a slurry with the free phytosterols crystallized in the slurry; and, washing and filtering the slurry to isolate the crystallized phytosterols.

25 Claims, 1 Drawing Sheet

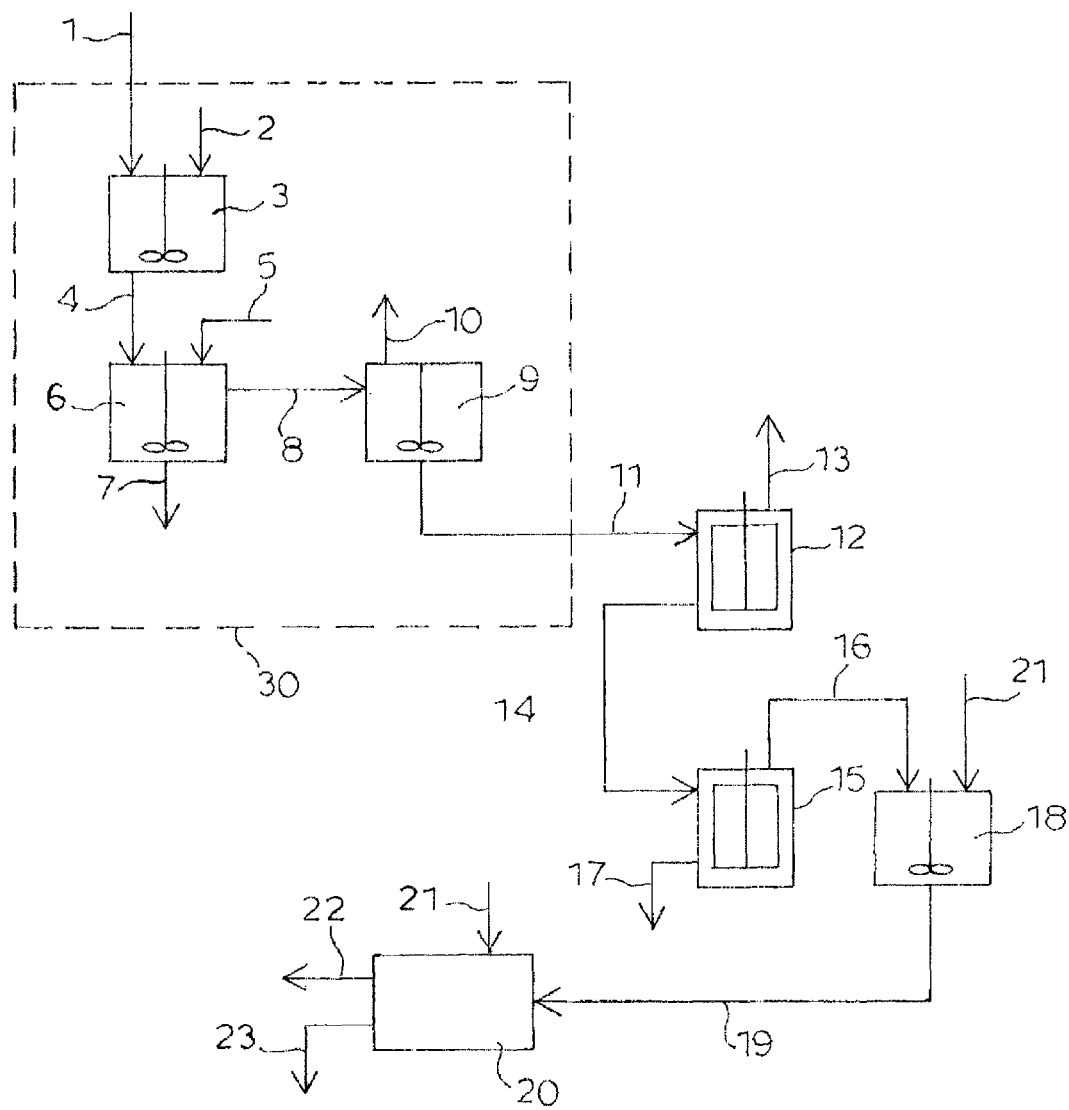

METHOD FOR THE PREPARATION OF PHYTOSTEROLS FROM TALL OIL PITCH

CROSS-REFERENCE

This application is a Continuation of prior U.S. patent application Ser. No. 12/233,392, filed Sep. 18, 2008, abandoned on Aug. 18, 2010, which is a Continuation of prior U.S. patent application Ser. No. 11/710,312, filed Feb. 23, 2007, abandoned on Sep. 29, 2008, which is a Continuation of prior U.S. patent application Ser. No. 11/313,581, filed Dec. 21, 2005, abandoned on Mar. 22, 2007, which is a Continuation of prior U.S. patent application Ser. No. 10/964,792, filed Oct. 14, 2004, abandoned on Jan. 31, 2006, which is a Continuation of prior U.S. patent application Ser. No. 10/630,572, filed Jul. 30, 2003, abandoned on Nov. 26, 2004, which is a Continuation of prior U.S. patent application Ser. No. 09/601,762, filed Aug. 7, 2000, abandoned on Sep. 22, 2003, which is a national stage completion (Rule 371) of prior PCT International Application No. PCT/CA99/00150, filed Feb. 19, 1999, which has priority to prior Canadian Patent Application Serial No. 2,230,373, filed Feb. 20, 1998. The benefit of the filing date of each prior application is hereby claimed for all purposes that are legally served by such claim for the benefit of the filing date.

FIELD OF THE INVENTION

The present invention relates to a method of preparing phytosterols from tall oil pitch, including the use of distillation techniques to isolate a phytosterol concentrate that can by crystallization yield high purity phytosterols using a solvent comprising alcohol or a combination of alcohols, and that may include water.

BACKGROUND TO THE INVENTION

Tall oil pitch is obtained from the black liquor of alkaline digestion of coniferous wood, most notably the kraft process. The black liquor is typically concentrated and settled to yield soap skimmings that contain sodium salts of fatty acids, sodium salts of resin acids and unsaponifiables. The latter group of substances include fatty alcohols, free sterols, steryl esters, and fatty acid esters. In kraft pulp mills, the collected soap is routinely acidulated with a mineral acid such as sulphuric acid to yield an oil phase and a water phase. The oil phase contains free fatty acids, resin acids and unsaponifiables; it is commonly known as crude tall oil. Typically, the amount of unsaponifiables can range from 10 to 35% by weight of the crude tall oil, depending on the species and quality of coniferous wood used. The water phase containing sodium sulphate and any lignin entrained in the original soap is normally recycled back to the pulp mill chemical recovery system. In the subsequent recovery of desired fatty acids and resin acids, crude tall oil is typically evaporated under low pressure conditions to yield a light phase, known as depitched tall oil, containing mainly fatty acids and resins, and a heavy phase, known as tall oil pitch, containing a small amount of fatty and rosin acids and a substantial amount of the original unsaponifiables.

Phytosterols can be isolated from either tall oil soap (sometimes referred to as soap skimmings) or from tall oil pitch. It is understood that the manufacture of sterols from tall oil soap has been practiced commercially by Oy Kaukas AB, Lppeenranta, Finland since 1981. The technologies are those based on the refining of tall oil soap with a combination of low molecular weight ketones, alcohols and hydrocarbons; for example, as disclosed by Holmbom et al. in U.S. Pat. No. 3,965,085 granted on 22 Jun. 1976. The refined tall oil soap is then extracted and crystallized using a combination of polar and non-polar solvents, for example, as taught by Johansson et al. in U.S. Pat. No. 4,044,031 granted on 23 Aug. 1977 and Hamunen in U.S. Pat. No. 4,422,974 granted on 27 Dec. 1983. Those methods of manufacture of pure tall oil sterols requires the soap skimmings to be relatively free of entrained black liquor and the use of multiple solvents which entails several separate solvent recovery systems. The adjustment of precise solvent compositions to maintain optimal operation for each processing stage is complex. In U.S. Pat. No. 4,153,622 granted on 8 May 1979, Lamminkari et al. disclose the use of acetone and activated carbon to extract sterols from tall oil soap, in which the acetone extract is subsequently evaporated for dissolution in ethanol for the final recovery of sterols.

The recovery of sterols from tall oil pitch has been studied for many years. In U.S. Pat. No. 2,715,638, Albrecht et al. teach the use of an amount of dilute alkaline solution to neutralize the fatty and rosin acids in tall oil pitch but in an amount to saponify the sterol ester. The remaining organic phase is then separated and saponified with an alcoholic alkaline solution to convert steryl esters into free sterols for subsequent dilution in hot water to precipitate the sterols by cooling. The product purity was indicated to be in the range of 83%. In U.S. Pat. Nos. 3,691,211 and 3,840,570 Julian teaches the use of a mixture of alcohol, water and hydrocarbon to extract tall oil pitch, then saponify the hydrocarbon phase with an alkali metal base, and finally dissolve the saponified material in a polar solvent for the recovery of phytosterols. The procedure is cumbersome as it involves several solvent extraction steps with different polar and non-polar solvents. The solvent recovery systems for at least polar and non-polar solvents are complex.

In U.S. Pat. No. 5,097,012 granted on 17 Mar. 1992, Thies et al. disclose a method for the isolation of sterols from crude tall oil by water extraction at elevated temperatures and pressures.

In U.S. Pat. No. 3,943,117 granted on 9 Mar. 1976, Force discloses a process for saponifying tall oil pitch in which a water-soluble cationic amine is used in conjunction with an alkali. In U.S. Pat. No. 4,524,024 granted on 18 Jun. 1985, Hughes teaches the hydrolysis of tall oil pitch at elevated temperatures to increase the recovery of fatty acids from tall oil pitch. In U.S. Pat. No. 3,887,537 granted on 3 Jun. 1975, Harada et al. disclose the recovery of fatty acids and rosin acids from tall oil pitch by first saponifying tall oil pitch with an alkali metal base and a low molecular weight alcohol, and then introducing the reacted mixture into a thin film evaporator to remove low-boiling matter such as water, alcohol use and light unsaponifiables. The bottom fraction from the first evaporator is next fed to a second thin film evaporator in which the unsaponifiables including sterols are removed as the light ends and a molten soap is recovered as the bottom fraction. Fatty acids and rosin acids are recovered from the molten soap fraction by acidulation conventionally with a mineral acid. In U.S. Pat. No. 3,926,936 granted on 16 Dec. 1975, Lebtinen teaches the recovery of fatty acids and rosin acids from tall oil pitch by reacting tall oil pitch with an alkali at 200 to 300 degrees Celsius, in the amount of 5 to 25% of tall oil pitch, prior to vacuum distillation of the heated mixture to recover the fatty acids and rosin acids in the distillate fraction.

Reference is also made to Chemical abstracts, vol. 112, no. 20, 14 May 1990, Columbus, Ohio US; abstract no. 181758, MALIK, Lubomir et al: "Isolation of phytosterols from tall—oil rosin", XP002104877 & CS 256 092 A (Czech). Malik et al. disclose a process for extracting phytosterols which includes the use of four distillation stages. Product flow is split into parallel distillation paths in a first distillation stage then, following further distillation in each parallel path, is partially recombined prior to a final distillation stage. To achieve high purity phytosterols, the output from the final distillation stage is subjected to two stages of crystallization utilizing relatively large amounts of solvent.

SUMMARY OF THE INVENTION

In a broad aspect of the present invention there is provided a new and improved method of preparing phytosterols from tall oil pitch containing steryl esters, the method comprising the steps of:
(a) converting the steryl esters to free phytosterols while in the pitch to produce a modified pitch containing the free phytosterols;
(b) distilling the modified pitch in a first evaporator to remove light ends from the modified pitch and produce a bottom fraction containing the free phytosterols;
(c) distilling only the bottom fraction in a second evaporator to produce a light phase distillate containing the free phytosterols;
(d) distilling only the light phase distillate in a solvent comprising an alcohol to produce a solution containing the free phytosterols;
(e) cooling the solution to produce a slurry with the free phytosterols crystallized in the slurry; and,
(f) washing and filtering the slurry to isolate the crystallized phytosterols.

Preferably, the step of converting the steryl esters to free phytosterols comprises the steps of saponifying the tall oil pitch with an alkali metal base, neutralizing the saponified pitch with an acid, and heating the neutralized pitch to remove water. The resulting pitch with such water removed defines the modified pitch.

Unlike the process of Malik et al., the foregoing process enables the preparation of high purity phytosterol crystals from tall oil pitch with only two distillation stages and only one stage of crystallization, and to do so with the use of a comparatively small amount of solvent. Nevertheless, it may be considered desirable in some cases to achieve phytosterol yields with even higher crystal purity. In accordance with another embodiment of the invention, a marginal improvement is achieved as follows:
(a) producing a light phase distillate containing free phytosterols in the manner described in steps (a) to (c) above;
(b) re-distilling only the light phase distillate so produced to enhance the concentration of free phytosterols in the light phase distillate;
(c) dissolving only the re-distilled light phase distillate in a solvent comprising an alcohol to produce a solution containing the free phytosterols; and,
(d) continuing the procedure as in steps (d) and (f) above to isolate crystallized phytosterols.

Although this procedure involves additional distillation steps, the amount of alcohol required during the crystallization stage remains small compared to the case of Malik et al.

BRIEF DESCRIPTION OF THE DRAWINGS

The FIGURE shows a schematic flow diagram for the preparation of high purity phytosterol crystals from tall oil pitch in accordance with the present invention.

DESCRIPTION OF PREFERRED EMBODIMENT

In accordance with the present invention, the isolation of phytosterols from tall oil pitch first requires converting steryl esters present in the pitch to free phytosterols while in the pitch. The result is a modified pitch containing free phytosterols.

It is contemplated that the required conversion may be accomplished by various methods. In the FIGURE, the conversion step is indicated by block 30 (shown in broken outline) which receives an incoming feed of tall oil pitch 1 and produces modified pitch 11 as an output. The presently preferred method of conversion involves the use of an alkali base treatment and is indicated by the elements contained within block 30.

As depicted within block 30, tall oil pitch 1 is added with an alkali metal base 2 into a reactor 3. The amount of alkali metal base relative to the tall oil pitch preferably should be sufficient to facilitate substantially complete saponification of the tall oil pitch.

Cost effectiveness considerations will generally favor the use of a water solution of an alkali metal base such as sodium hydroxide, potassium hydroxide or a combination thereof. These compounds or combinations will provide a relatively high alkalinity for a relatively reasonable cost. If such compounds or combinations are used, then the stoichiometric proportion of alkali metal base 2 to tall oil pitch 1 that theoretically is required to achieve complete conversion typically may be in the neighborhood of about 1% by weight. Of course, the precise amount will depend upon the specific characteristics of tall oil pitch 1, and these characteristics may vary from one batch of feed or source to another. As well, and again depending upon the specific characteristics of tall oil pitch 1, it will be recognized that a significant portion of alkali metal base 2 may be consumed by reaction with constituents of pitch 1 other than steryl esters. Accordingly, to provide a strong driving force for the reaction, and to better ensure efficient conversion of the steryl esters that are present, a significantly higher proportion of alkali metal base 2 to tall oil pitch 1 may be considered desirable. Typically, this proportion may be in the range of 5 to 15% by weight.

Mixing is sustained in reactor 3 with sufficient to vigor to maintain contact between pitch 1 and alkali metal base 2. Typically, an operating temperature in the range of 100 to 250 deg. C. for a period in the range of 60 minutes (at the higher temperature) to 300 minutes (at the lower temperature) will suffice to facilitate the desired saponification.

Following saponification in reactor 3, the saponified pitch 4 is discharged into a second reactor 6. An acid 5 is also added to reactor 6.

Acid 5 may be a simple organic acid such as acetic acid or formic acid, both of which are commercially practical. As well, acid 5 may be a mineral acid such as sulphuric acid, hydrochloric acid or phosphoric acid. These are relatively strong mineral acids and are favored over weaker acids such as boric acid. Nitric acid is a possibility. However, it is contemplated that undesirable nitration may occur.

Sufficient acid 5 is added to reactor 6 such that the mixture reaches a water phase pH between 4 and 7, and preferably between 5 and 7. Although the mixture should be monitored during the additive process, the latter typically will be achieved when the amount of acid is about 20% in excess of the stoichiometric amount required for the neutralization of the residual alkali metal base present in saponified pitch 4.

With gentle stirring in reactor 6, an operating temperature in the range of 10 to 100 deg. C. for a period in the range of 1 hour (at the higher temperature) to 10 hours (at the lower temperature) will typically suffice to facilitate the desired neutralization. Then, with continued gentle stirring, the mixture in reactor 6 is maintained at a temperature of about 95 deg. C. for approximately 120 minutes to effect the bulk disengagement of water from the organic phase. Excess water 7 is drawn off and the resulting neutralized pitch 8 is introduced into a third reactor 9 for further processing.

Notwithstanding the removal of excess water 7 in reactor 6, a relatively high water content may still subsist By heating mixture 8 in reactor 9, preferably under vacuum conditions, water 10 is further stripped off to produce a modified pitch 11 containing free phytosterols and preferably comprising less than 1% by weight water.

Modified pitch 11 is introduced into an ultra-low pressure evaporator 12 operating in the range of 0.1 to 10 millibars pressure (but preferably not more than 1 millibar) and at a temperature in the range of 160 to 280 deg. C., for the removal of 1 to 15% of light ends 13 in the modified pitch. These light ends will comprise a high proportion of the fatty and resin acids found in the original tall oil pitch 1.

The bottom fraction 14 of modified pitch 11 contains the free phytosterols and is removed from evaporator 12 and introduced into a second ultra-low pressure wiped film evaporator 15. Evaporator 15 serves to distill free phytosterols present in fraction 14 into a light phase distillate 16. To do so efficiently, it preferably is operated at a pressure in the range of 0.01 to 1.0 millibars pressure and at a temperature in the range of 180 to 300 deg. C. Distillate 16 also contains fatty alcohols, fatty acids, rosin acids and high molecular weight wax esters. A bottom fraction 17 is discarded and may be used as a waste fuel or feedstock for other industries.

Distillate 16 is introduced into a further reactor 18 where it is heated and stirred until dissolution has occurred in an added solvent 21. Solvent 21 includes alcohol, preferably a low molecular weight monohydric alcohol such as methanol, ethanol or 2-propanol, or a combination of such alcohols. As well, the solvent may include water.

Effective dissolution of free phytosterols has been found to occur at about 65 deg. C. Other temperatures may of course be used, but it has to be borne in mind that the solubility of the phytosterols will decrease as the temperature is lowered When dissolution has occurred, the solution is cooled in reactor 18 together with high speed mixing to produce a slurry 19 with free phytosterols crystallized in the slurry. Typically, the temperature at which crystallization is effected may be in the range of 0 to 35 deg. C.

The cooled slurry 19 is washed and filtered to dryness with a filtration apparatus 20 advantageously using added solvent 21 like that used in reactor 18. The result is a yield of high purity phytosterol crystals 22 and spent solvent filtrate 23, the latter of which may be recovered for recycling and reuse.

In more detail, the practice of the invention may be seen from the following examples:

EXAMPLE 1

9,598 kg of tall oil pitch were saponified with 1,325 kg NaOH at 12.0% concentration solution, at 146 deg. C. for 120 minutes, under vigorous mixing conditions. The weight ratio of sodium hydroxide (dry basis) to tall oil pitch was 0.138. The reacted mixture was then neutralized with 1,188 kg of 85% concentration phosphoric acid. After continued heating at 146 deg. C. and gentle stirring for 210 minutes, 6,600 kg of water was drawn off from the bottom of the reactor. The pH of the reactor bottom water was 6.4. The partially dewatered mixture containing about 37.5% water was transferred to a second reactor for vacuum stripping of residual moisture. The vacuum reactor was operated at 149 deg. C. at an average pressure of 300 mm Hg. The reaction was completed in 300 minutes. The dried, saponified and neutralized tall oil pitch had a moisture content of 0.4% by wt.

Table 1 summarizes the percentage of phytosterols present in free form at various stages in the procedure.

TABLE 1

| Processing Stage | % phytosterols in free form |
|---|---|
| Tall oil pitch feed | 26.8 |
| After saponification | 83.0 |
| After neutralization | 81.0 |
| After vacuum stripping | 84.6 |

The phytosterols mostly in free from are now ready for separation from the modified tall oil pitch.

EXAMPLE 2

A sample of tall oil pitch was saponified, neutralized and dewatered by the method described in Example 1. The modified tall oil pitch was found to have a composition of 141 mg free phytosterols/g and 164 mg total phytosterols/g. The modified tall oil pitch was preheated to about 100 deg. C. for feeding into a series of 0.1 square meter wiped evaporators (manufactured by UIC GmbH, Germany). The distillate from each evaporation stage was recovered for the analysis of free phytosterols by gas-liquid chromatography (GLC).

Table 2 summarizes free phytosterol production results for four tests runs (A1, A2, A3 and A4) under differing conditions of feed rate, temperature and pressure.

TABLE 2

| | Test Number | | | |
|---|---|---|---|---|
| | A1 | A2 | A3 | A4 |
| Stage 1 Evaporation | | | | |
| Tall oil pitch feed, kg/hr | 15.5 | 15.6 | 11.5 | 15.6 |
| Temperature, deg. C. | 225 | 225 | 225 | 220 |
| Pressure, mbar | 5.94 | 6.53 | 6.45 | 2.08 |
| Distillate yield, % by wt. | <1 | <1 | <1 | 1.90 |
| Free phytosterols in Stage 1 distillate, mg/g | 18 | 18 | 18 | 18 |
| Stage 2 Evaporation | | | | |
| Feed from above Stage 1 residue, kg/hr | 15.6 | 15.6 | 11.5 | 15.3 |
| Temperature, deg. C. | 251 | 269 | 252 | 265 |
| Pressure, mbar | 0.32 | 0.37 | 0.07 | 0.07 |
| Distillate yield, % by wt. relative to Stage 1 feed | 40.4 | 49.7 | 49.6 | 51.2 |
| Free phytosterols in Stage 2 distillate, mg/g | 248 | 250 | 254 | 262 |
| Free phytosterols recovered in Stage 2 distillate, % of free phytosterols present in tall oil pitch | 71.1 | 88.1 | 89.4 | 94.8 |

EXAMPLE 3

Samples of Stage 2 distillate from Example 2 were crystallized in laboratory jar tests by heating the distillate-solvent mixture to 65 deg. C. The mixtures were cooled to 30 to 35 deg. C. to yield a slurry containing the desired phytosterol crystals. The weight ratio of organic solvent to distillate was 15:1.0. The cooled slurry was then filtered through 50 micrometer filter paper, under vacuum. The filtered cake was then washed twice with solvent in an amount equal to 1.5 times the weight of distillate sample used for crystallization. The wash solvent had the same composition as that used for crystallization. Washing of the cake was conducted at ambient temperature. The washed cake was then dried at 90 deg. C. for 60 minutes prior to weighing and GLC analysis.

Table 3 comparatively summarizes crystal purities and crystal yields for test runs A1, A2, A3 and A4, firstly, utilizing methanol as the solvent and, secondly, utilizing a mixture of methanol and 2-propanol as the solvent.

TABLE 3

|  | Stage 2 Distillate Test Number | | | |
|---|---|---|---|---|
|  | A1 | A2 | A3 | A4 |
| Solvent: 100% methanol | | | | |
| Crystal purity, mg pure phytosterols/g dry cake | 983 | 970 | 956 | 933 |
| Crystal yield, % based on phytosterols in test distillate | 41.9 | 43.2 | 46.3 | 48.0 |
| Solvent: 70% methanol and 30% 2-propanol | | | | |
| Crystal purity, mg pure phytosterols/g dry cake | 1000 | 972 | 997 | 997 |
| Crystal yield, % based on phytosterols in test distillate | 30.5 | 31.9 | 33.8 | 38.6 |

EXAMPLE 4

A sample of Stage 2 distillate from Test Number A4 was re-distilled further in a wiped film evaporator. The distillate feed had a composition of 262 mg free phytosterols/g and 264 mg total phytosterols/g. The feed was pre-heated to about 100 deg. C. for feeding into the 0.1 square meter wiped film evaporator (manufactured by UIC GmbH, Germany). The distillate samples were recovered for the analysis of free phytosterols by gas-liquid chromatography (GLC).

Table 4 summarizes free phytosterol production results for four tests runs (B1, B2, B3 and B4) under differing conditions of feed rate, temperature and pressure.

TABLE 4

|  | Test Number | | | |
|---|---|---|---|---|
|  | B1 | B2 | B3 | B4 |
| Distillate feed, kg/hr | 8.7 | 8.7 | 15.1 | 14.9 |
| Temperature, deg. C. | 216 | 230 | 240 | 249 |
| Pressure, mbar | 0.16 | 0.15 | 0.29 | 0.26 |
| Distillate yield, % by wt. | 74.4 | 85.6 | 79.8 | 86.4 |
| Free phytosterols in distillate, mg/g | 248 | 275 | 260 | 266 |
| Free phytosterols recovered from distillate feed, % by wt. | 70.7 | 91.2 | 80.4 | 88.4 |

EXAMPLE 5

Distillate samples from Example 4 were collected for laboratory scale crystallization using the procedure described previously in Example 3. The solvent used was 100% methanol. Table 5 comparatively summarizes crystal purities and crystal yields for test runs B1, B2, B3 and B4.

TABLE 5

|  | Stage 3 Distillate Test Number | | | |
|---|---|---|---|---|
|  | B1 | B2 | B3 | B4 |
| Crystal purity, mg pure phytosterols/g dry cake | 992 | 972 | 986 | 978 |
| Crystal yield, % based on phytosterols in test distillate | 36.9 | 40.7 | 37.9 | 44.8 |

EXAMPLE 6

Distillate from Stage 3, distillation Test Number B4, was crystallized using other mixtures of alcohol or alcohol and water. The test procedure was identical to that described in Example 3. The free phytosterol content of test distillate was 266 mg/g.

Table 6 comparatively summarizes crystal purities and crystal yields for five test runs C1, C2, C3, and C4.

TABLE 6

|  | Stage 3 Distillate Test No. B4 | | | |
|---|---|---|---|---|
|  | C1 | C2 | C3 | C4 |
| Methanol, % by wt. | 15.0 | 12.6 | 70 | 58.7 |
| Ethanol, % by wt. | 85.0 | 71.3 | 0.0 | 0.0 |
| 2-propanol, % by wt. | 0.0 | 0.0 | 30.0 | 25.1 |
| Water, % by wt. | 0.0 | 16.1 | 0.0 | 16.2 |
| Crystal purity, mg pure phytosterols/g dry cake | 999 | 985 | 991 | 975 |
| Crystal yield, % based on phytosterols in test distillate | 34.4 | 46.3 | 39.1 | 58.0 |

EXAMPLE 7

Distillate from Stage 3 distillation Test Number B4 was again crystallized in the laboratory using alcohols, and the test procedure was again identical to that described in Example 3, except that the crystallization was conducted at 0 deg. C. The weight ratio of organic solvent to distillate was varied. Wash solvent was maintained at ambient temperature. The free phytosterol content of test distillate was 266 mg/g.

Table 7 comparatively summarizes crystal purities and crystal yields for two test runs D1 and D2 utilizing the same methanol-ethanol solvent, but with different proportions of solvent to distillate.

TABLE 7

|  | Stage 3 Distillate Test No. B4 | |
|---|---|---|
|  | D1 | D2 |
| Methanol, % by wt. | 15.0 | 15.0 |
| Ethanol, % by wt. | 85.0 | 85.0 |
| Proportion of solvent to distillate, by wt. | 1.6 | 3.0 |
| Crystal purity, mg pure phytosterols/g dry cake | 983 | 965 |
| Crystal yield, % based on phytosterols in test distillate | 66.3 | 66.6 |

As noted above, it is contemplated that the conversion of steryl esters present in tall oil pitch 1 to free phytosterols while in the pitch may be accomplished by various methods. The method described involves the use of an alkali base treatment. Although experimentation may be required, and although there may be difficulties, other methods that may be tried include water hydrolysis treatment and acid hydrolysis treatment of the tall oil pitch.

We claim:

1. A method of preparing phytosterols from tall oil pitch containing steryl esters, said method comprising the steps of:
   (a) converting said steryl esters to free phytosterols while in said pitch to produce a modified pitch containing said free phytosterols including the steps of
      (i) saponifying said tall oil pitch with an alcohol-free solution consisting essentially of water containing an alkali metal base,
      (ii) neutralizing said saponified pitch with an acid, and
      (iii) treating said neutralizing pitch to remove water, the resulting pitch with such water removed defining said modified pitch;
   (b) distilling said modified pitch in a first evaporator to remove light ends from said modified pitch and produce a bottom fraction containing said free phytosterols;
   (c) distilling only said bottom fraction in a second evaporator to produce a light phase distillate containing said free phytosterols;
   (d) dissolving said light phase distillate in a solvent comprising an alcohol to produce a solution containing said free phytosterols;
   (e) cooling said solution to produce a slurry with said free phytosterols crystallized in said slurry; and,
   (f) washing and filtering said slurry to isolate said crystallized phytosterols.

2. A method as defined in claim 1, wherein said modified pitch comprises less than 1% water by weight.

3. A method as defined in claim 1 or 2, wherein said solvent comprises a low molecular weight monohydric alcohol.

4. A method as defined in claim 1 or 2, wherein said solvent comprises a low molecular weight monohydric alcohol and water.

5. A method as defined in claim 1 or 2, wherein said slurry is washed and filtered using a solvent comprising an alcohol.

6. A method as defined in claim 1, wherein said step of treating said neutralized pitch to remove water in step (a)(iii) comprises: heating said neutralized pitch to remove water, the resulting pitch with such water removed defining said modified pitch.

7. A method as defined in claim 6, wherein said alkali metal base is selected from the group consisting of:
   (a) sodium hydroxide;
   (b) potassium hydroxide;
   (c) sodium hydroxide and potassium hydroxide.

8. A method as defined in claim 7, wherein in the weight percentage of alkali metal base to tall oil pitch is in the range of 1% to 15%.

9. A method as defined in claim 7, wherein said saponification is conducted at a temperature in the range of 100 to 250 deg. C. for a period in the range of 60 to 300 minutes.

10. A method as defined in claim 6, wherein said acid is an organic acid.

11. A method as defined in claim 6, wherein said acid is a mineral acid.

12. A method as defined in claim 11, wherein said mineral acid is selected from the group consisting of:
   (a) sulphuric acid;
   (b) hydrochloric acid;
   (c) phosphoric acid;
   (d) a combination of acids comprising two or more of sulphuric acid, hydrochloric acid and phosphoric acid.

13. A method as defined in claim 6, wherein said neutralization is conducted at a temperature in the range of 10 to 100 deg. C. for a period in the range of 1 to 10 hours.

14. A method as defined in claim 6, wherein said neutralized pitch has a water phase pH in the range of 4 to 7.

15. A method as defined in claim 6, wherein said heating step comprises heating at a temperature in the range 90 to 100 deg. C. for a time sufficient to effect the bulk disengagement of water from the organic phase.

16. A method as defined in claim 15, wherein said heating step further comprises heating under vacuum conditions such that said modified pitch comprises less than 1% water by weight.

17. A method as defined in claim 1 or 6, wherein said light ends are removed in a wiped film evaporator operating at a pressure in the range of 0.1 to 10 millibars and at a temperature in the range 160 to 280 deg. C.

18. A method as defined in claim 1 or 6, wherein said bottom fraction is evaporated in a wiped film evaporator operating at a pressure in the range of 0.01 to 1.0 millibars and at a temperature in the range 180 to 300 deg. C.

19. A method as defined in claim 6, wherein said solvent comprises a low molecular weight monohydric alcohol.

20. A method as defined in claim 6, wherein said solvent comprises a low molecular weight monohydric alcohol and water.

21. A method as defined in claim 1 or 6 in which the crystallization of phytosterols is effected at a temperature in the range of 0 to 35 deg. C.

22. A method of preparing phytosterols from tall oil pitch containing steryl esters, said method comprising the steps of:
   (a) converting said steryl esters to free phytosterols while in said pitch to produce a modified pitch containing said free phytosterols including the steps of
      (i) saponifying said tall oil pitch with an alcohol free solution consisting essentially of water containing an alkali metal base,
      (ii) neutralizing said saponified pitch with an acid, and
      (iii) treating said neutralizing pitch to remove water, the resulting pitch with such water removed defining said modified pitch;
   (b) distilling said modified pitch in a first evaporator to remove light ends from said modified pitch and produce a bottom fraction containing said free phytosterols;
   (c) distilling only said bottom fraction in a second evaporator to produce a light phase distillate containing said free phytosterols;
   (d) re-distilling only said light phase distillate to enhance the concentration of free phytosterols in said light phase distillate;
   (e) dissolving only said re-distilled light phase distillate in a solvent comprising an alcohol to produce a solution containing said free phytosterols;
   (f) cooling said solution to produce a slurry with said free phytosterols crystallized in said slurry; and,
   (g) washing and filtering said slurry to isolate said crystallized phytosterols.

23. A method as defined in claim 22, wherein said solvent further comprises water added in a proportion up to 35% by weight relative to the organic solvent phase.

24. A method as defined in claim 23, wherein the weight ratio of solvent to distillate is between 0.3 to 2.0.

25. A process according to claim 19, 20 or 24 in which the alcohol is selected from:
   (a) methanol;
   (b) ethanol;
   (c) 2-propanol;
   (d) a combination of alcohols comprising two or more of methanol, ethanol and 2-propanol.

* * * * *